(12) United States Patent
Ennifar

(10) Patent No.: US 7,446,205 B2
(45) Date of Patent: Nov. 4, 2008

(54) METHOD FOR MAKING NICOTINE HAPTEN

(75) Inventor: Sofiane Ennifar, Silver Spring, MD (US)

(73) Assignee: Nabi Biopharmaceuticals, Rockville, MD (US)

( * ) Notice: Subject to any disclaimer, the term of this patent is extended or adjusted under 35 U.S.C. 154(b) by 57 days.

(21) Appl. No.: 11/600,317

(22) Filed: Nov. 16, 2006

(65) Prior Publication Data

US 2007/0129551 A1 Jun. 7, 2007

Related U.S. Application Data

(60) Provisional application No. 60/739,933, filed on Nov. 28, 2005.

(51) Int. Cl.
*C07D 401/04* (2006.01)
(52) U.S. Cl. .................................... 546/276.4
(58) Field of Classification Search ............... 546/276.4
See application file for complete search history.

(56) References Cited

U.S. PATENT DOCUMENTS 5,278,176 A 1/1994 Lin

OTHER PUBLICATIONS

Pozdnev, "Activation of Carboxylic Acids by Pyrocarbonates," *Tetrahedron Letters*, Sep. 25, 1995, pp. 7115-7118, vol. 36.
Zhai et al., "Development and validation of HPLC methods for enantiospeartion of mirtazapine enantiomers at analytical and semipreparative scale using polysaccharide chiral stationary phases," *Analytica Chimica Acta*, Sep. 26, 2005, pp. 123-129, vol. 550, Issues 1-2.

*Primary Examiner*—Patricia L Morris
(74) *Attorney, Agent, or Firm*—Foley & Lardner LLP

(57) ABSTRACT

A high yielding and short process for preparing the 3'-aminomethylnicotine hapten of general formula I

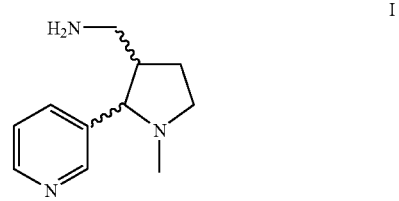

permits the isolation of the hapten in very pure quantities. The process can be adapted for the synthesis of a single stereoisomer or mixtures of stereoisomers, such as the stereoisomers trans-Ia and trans-Ib:

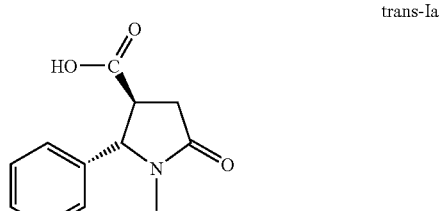

trans-Ia

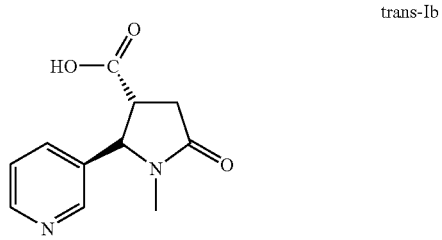

trans-Ib

Compounds of general formula I are useful for the preparation of hapten-carrier conjugates in the treatment of nicotine addiction.

15 Claims, No Drawings

METHOD FOR MAKING NICOTINE HAPTEN

CROSS-REFERENCE TO RELATED PATENT APPLICATIONS

This application claims priority from Provisional Application 60/739,933, filed Nov. 28, 2005, incorporated herein by reference in its entirety.

BACKGROUND OF THE INVENTION

The present invention relates to methods of producing stereochemically pure 3'-aminomethylnicotine haptens. The haptens are useful for making hapten-carrier conjugates which are capable of inducing the production of antibodies. Such antibodies are capable of specifically binding to nicotine.

Smoking of cigarettes, cigars, and pipes is a prevalent problem in the United States and worldwide. Smoking tobacco and smokeless tobacco are rich in nicotine, which is a known addictive substance. Nicotine is an alkaloid derived from the tobacco plant that is responsible for the psychoactive and addictive effects of smoking. Nicotine is formed of two rings linked together by a single bond: an aromatic six-membered ring (pyridine) and an aliphatic five-membered ring (pyrrolidine). The pyrrolidine is N-methylated and linked through its carbon-2 to the carbon-3 of the pyridine ring. Thus, the carbon-2 is chiral, and there is virtually free rotation around the single bond linking the two rings. It has been established that the absolute configuration of carbon-2 is S. Thus, the natural configuration of nicotine is (S)-(−)-nicotine.

Nicotine use is widespread due to the easy availability of cigarettes, cigars, pipes and smokeless tobacco. According to the U.S. Department of Health and Human Services, cigarette smoking is the single leading cause of preventable death in the United States. See also McGinnis et al., *J. Am. Med. Assoc.,* 270, 2207-2211 (1993). Exposure to second hand smoke also has been reported to have serious detrimental health effects, including exacerbation of asthma.

Even though the addictive nature of nicotine is well known, cigarette smoking is prevalent. Peak levels of nicotine in the blood—about 25 to 50 nanograms/ml—are achieved within 10-15 minutes of smoking a cigarette. In humans, smoking a cigarette results in arterial nicotine concentrations being 10-fold higher than venous nicotine concentrations because nicotine is rapidly delivered from the lungs to the heart (see Henningfield, *Drug Alcohol Depend.,* 33, 23-29 (1993)). This results in a rapid delivery of high arterial concentrations of nicotine to the brain. Once nicotine crosses the blood-brain barrier, evidence suggests that it binds to cholinergic receptors, which are normally activated by the neurotransmitter acetylcholine, which is involved in respiration, maintenance of heart rate, memory, alertness and muscle movement. When nicotine binds to these receptors, it can affect normal brain function, by triggering the release of other neurotransmitters, such as dopamine. Dopamine is found in the brain in regions involved in emotion, motivation, and feelings of pleasure. It is the release of neurotransmitters, especially dopamine, that is responsible for the tobacco user's addiction to nicotine or other intake of nicotine.

Due to the significant adverse effects of smoking on health, smokers often try to quit. However, the addictive nature of nicotine and the availability of cigarettes add to the continued dependence on nicotine and high failure rate of those who try to quit. Withdrawal symptoms are unpleasant, and they are relieved by smoking.

Many therapies for nicotine addiction have been developed, but are largely ineffective. The two most popular therapies remain the nicotine transdermal patch and nicotine incorporated into chewing gum. These therapies, termed "nicotine replacement therapies" (NRT), replace the amount of nicotine which the user previously received from smoking and act to wean the user off nicotine. However, certain drawbacks are seen with this type of therapy. Particularly, there is low penetration of nicotine into the bloodstream and therefore an increased desire to smoke. Problems such as mouth irritation, jaw soreness, nausea, have been associated with use of nicotine chewing gum. Problems such as skin irritations, sleep disturbance, and nervousness have been associated with use of nicotine transdermal patches.

Therefore, an alternative methodology for treating nicotine addiction is needed. The literature documents this need and the several attempts to provide a methodology for treating nicotine addiction. One of the methods involves the administration of antibodies which have been raised in response to nicotine. However, low molecular weight substances, called haptens, are known to be unable to trigger an immune response in host animals. Nicotine is no exception, and as a small molecule it is not immunogenic. To elicit an antibody response to a hapten, it typically is covalently bound to a carrier protein, and the complex will elicit the production of antibodies that recognize the hapten.

For example, cotinine 4'-carboxylic acid, when bound covalently to keyhole limpet hemocyanin (KLH) was used to generate antibodies to the nicotine metabolite cotinine. Those antibodies were used to determine the presence of cotinine in physiological fluids. See Bjerke et al. *J. Immunol. Methods,* 96, 239-246 (1987).

Other nicotine antibodies were prepared by Castro et al., (*Eur. J. Biochem.,* 104, 331-340 (1980)). Castro et al. prepared nicotine haptens, conjugated to bovine serum albumin (BSA), via a linker at the 6-position of nicotine. Castro et al. prepared additional nicotine conjugates of BSA which were injected into mammals to raise antibodies. In another publication, Castro et al. in *Biochem. Biophys. Res. Commun.* 67, 583-589 (1975) disclose two nicotine albumin conjugates: N-succinyl-6-amino-(±)-nicotine-BSA and 6-(σ-aminocapramido)-(±)-nicotine-BSA. In this 1975 publication, Castro et al. also used antibodies to nicotine carrier conjugate, 6-(σ-aminocapramido)-(±)-nicotine-BSA, to determine the levels of nicotine in blood and urine, see *Res. Commun Chem. Path. Pharm.* 51, 393-404 (1986).

Swain et al. (WO 98/14216) disclose nicotine carrier conjugates wherein the hapten is conjugated at the 1, 2, 4, 5, 6, or 1' position of the nicotine. Hieda et al. have shown that animals immunized with 6-(carboxymethylureido)-(±)-nicotine, which was linked to keyhole limpet hemocyanin, produced antibodies specific to nicotine. *J. Pharmacol. Exper. Ther.* 283, 1076-1081 (1997). Langone et al. prepared the hapten derivative, O-succinyl-3'-hydroxymethyl-nicotine, see *Biochemistry,* 12, 5025-5030 (1973), and used the antibodies to this hapten carrier conjugate in radioimmunoassays. See *Methods in Enzymology,* 84, 628-635 (1982). The conjugate produced by Langone is susceptible to hydrolysis. Additionally, Abad et al. in *Anal. Chem.,* 65, 3227-3231 (1993) describe conjugating the same 3'-hydroxymethyl-nicotine hemisuccinate to bovine serum albumin to produce antibodies to nicotine in order to be able to measure nicotine content in smoke condensate of cigarettes in an ELISA assay.

A more recent advance was described in U.S. Pat. No. 6,232,082, which provides hapten-conjugates where the hapten is an enantiomerically pure 3'-aminomethyl nicotine. The hapten, however, must first be synthesized utilizing a five step procedure starting with a commercially available nicotine derivative. It would be commercially desirable to employ a shorter, more convenient and efficient synthesis of this hapten.

SUMMARY OF THE INVENTION

The invention satisfies this need and others by providing as one embodiment a process for the preparation of a compound of general formula I:

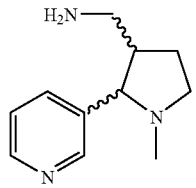

I

The process comprises the step of reacting a compound of general formula

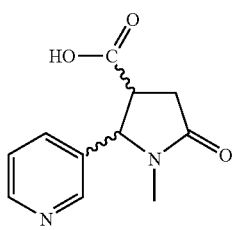

II with an amidating reagent to yield a compound of general formula III:

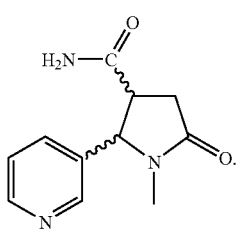

III

The process further comprises reacting the compound of general formula III with a reducing agent to yield said compound of general formula I.

Another embodiment provides a process for the preparation of a racemic mixture of compounds of formulae trans-Ia and trans-Ib:

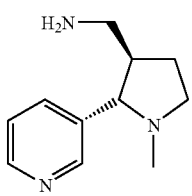

trans-Ia

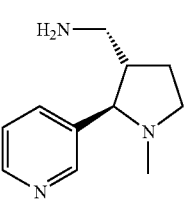

trans-Ib

The process comprises the step of reacting a racemic mixture of compounds of general formulae trans-IIa and trans-IIb:

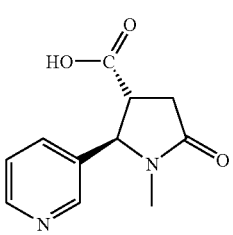

trans-IIa

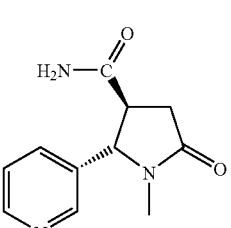

trans-IIb with an amidating reagent to yield a racemic mixture of compounds of formulae trans-IIIa and trans-IIIb:

trans-IIIa

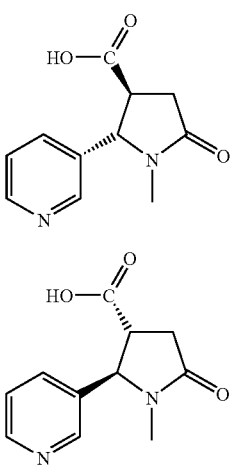

trans-IIIb

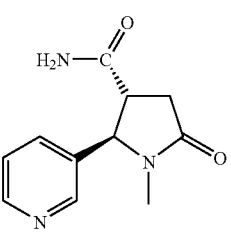

The process further comprises reacting the racemic mixture of compounds of formulae trans-IIIa and trans-IIIb with a reducing agent to yield the racemic mixture of compounds of formulae trans-Ia and trans-Ib.

In another embodiment, the invention provides a further process for the preparation of a racemic mixture of compounds of formulae trans-Ia and trans-Ib, as depicted above.

In this embodiment, the process comprises the steps of reacting a racemic mixture of compounds of general formulae trans-IIa and trans-IIb, as depicted above, with an amidating reagent comprising ammonium bicarbonate and di-t-butyl dicarbonate to yield a racemic mixture of compounds of general formulae trans-IIIa and trans-IIIb, as shown above. The resultant racemic mixture of compounds of general formulae trans-IIIa and trans-IIIb is reacted with sodium bis(2-methoxyethoxy)aluminum hydride to yield the racemic mixture of compounds of formulae trans-Ia and trans-Ib. The process also comprises purifying the racemic mixture of compounds of formulae trans-Ia and trans-Ib by subjecting the mixture to preparative high performance liquid chromatography.

DETAILED DESCRIPTION

The inventors discovered processes of efficiently producing 3'-aminomethylnicotine in commercially useful quantities. This result can be achieved in part because the processes described feature fewer synthetic steps and an overall higher yield compared to conventional processes known in the art. Furthermore, the processes can be tailored to produce optically pure quantities of 3'-aminomethylnicotine as described more fully below. 3'-Aminomethylnicotine is useful as a hapten for making hapten-carrier protein conjugates as described, for example, in U.S. Pat. No. 6,232,082. In particular, the nicotine haptens made using the methods of the present application contain a reactive functional group, to which the carrier protein can be attached directly, or via a linker, or via a matrix, or via a linker and a matrix. Such a carrier proteins can be any suitable immunogenic protein or polypeptide. Preferably the carrier protein comprises a T-cell epitope. Examples of suitable carrier proteins include, but are not limited to, toxins of pathogenic bacteria and their toxoids. Examples include diphtheria and tetanus toxins and their medically acceptable corresponding toxoids. Examples of other carrier proteins known in the art are proteins antigenically similar to bacterial toxins referred to as cross-reacting materials (CRMs), virus like particles (VLPs), other viral subunits. Recombinant *Pseudomonas aeruginosa* exoprotein A (rEPA) may be used as a carrier protein because its structure and biological activities have been well characterized. One type of exoprotein A is described in Fattom et al., Infect Immun. 61 1023-1032 (1993). This protein has been identified as a suitable protein carrier because the intrinsic enzymatic activity of the native exotoxin has been eliminated due to an amino acid deletion at position 553. As a result, rEPA has the same immunological profile as the native exotoxin A (ETA), but does not possess the hepatotoxic properties of the native ETA. As used in this application, "exoprotein A" refers to a modified, non-hepatotoxic, ETA. One example of such an exoprotein A has an amino acid deletion at position 553.

The term "epitope" includes any determinant on an antigen that is responsible for its specific interaction with an antibody molecule. Epitope determinants usually consist of chemically active surface groupings of molecules such as amino acids or sugar side chains and have specific three dimensional structural characteristics as well as specific charge characteristics.

The 3'-aminomethylnicotine molecule possesses two chiral centers designated as C-2' and C-3' as shown below:

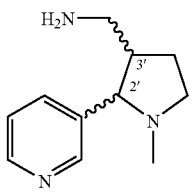

Consequently, a given 3'-aminomethylnicotine molecule can exist as one of the following four possible stereoisomers:
- ((2S,3R)-1-methyl-2-(pyridine-3-yl)pyrrolidin-3-yl)methanamine (trans-Ia),
- ((2R,3S)-1-methyl-2-(pyridine-3-yl)pyrrolidin-3-yl)methanamine (trans-Ib),
- ((2S,3S)-1-methyl-2-(pyridine-3-yl)pyrrolidin-3-yl)methanamine, and
- ((2R,3R)-1-methyl-2-(pyridine-3-yl)pyrrolidin-3-yl)methanamine.

The configurations 2S,3R and 2R,3S of the first two stereoisomers place the 3-pyridyl and 2-aminomethyl substituents in a trans orientation to each other, while the 2S,3S and 2R,3R configurations of the last two impose cis orientations of these substituents. As defined herein, accordingly, the compound of formula trans-Ia is ((2S,3R)-1-methyl-2-(pyridine-3-yl)pyrrolidin-3-yl)methanamine, and the related stereoisomer of formula trans-Ib is ((2R,3S)-1-methyl-2-(pyridine-3-yl)pyrrolidin-3-yl)methanamine.

In one embodiment, the invention provides a process for the preparation of a compound of general formula I:

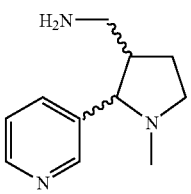

I

The skilled artisan will appreciate that the wavy lines reflect general formula I as encompassing all four stereoisomers of 3'-aminomethylnicotine. Thus, formula I contemplates a single stereoisomer as well as all possible mixtures of two or more stereoisomers. For example, general formula I may comprise a racemic mixture of trans-Ia and trans-Ib.

In this embodiment, the process commences with the amidation of a compound of general formula II:

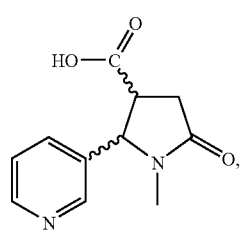

II which is a commercially available compound. The wavy lines in general formula II and herein throughout convey the same meaning as described above for general formula I. The amidation reaction can employ any convenient amidating reagent that is common to such organic transformations to yield a compound of general formula III:

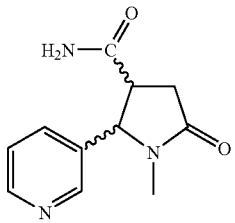

III

Reduction of the compound of general formula III by any suitable reducing agent yields the compound of general formula I.

In some embodiments, the process further comprises purifying the compound of general formula III. Purification, as defined herein, refers to not only separating the desired compound or compound mixture from impurities, but also to separating a desired stereoisomer or mixture of stereoisomers from other stereoisomers. Thus, a compound of general formula III can be purified as a mixture of two or more stereoisomers, or as a single stereoisomer. In the latter scenario, for example, chiral high performance liquid chromatography (HPLC) can be used to isolate any one of ((2S,3R)-1-methyl-2-(pyridine-3-yl)pyrrolidin-3-yl)methanamine (trans-Ia), ((2R,3S)-1-methyl-2-(pyridine-3-yl)pyrrolidin-3-yl)methanamine (trans-Ib), ((2S,3S)-1-methyl-2-(pyridine-3-yl)pyrrolidin-3-yl)methanamine, and ((2R,3R)-1-methyl-2-(pyridine-3-yl)pyrrolidin-3-yl)methanamine from crude product mixtures containing one or more of these stereoisomers. All of these combinations are contemplated. Typical purities of the desired compound or stereochemical mixtures thereof are at least 90, 95%, 98%, and 100% as determined, for example, by HPLC.

In yet other embodiments, the process further comprises isolating the compound of general formula III as a racemic mixture of compounds of formulae trans-Ia and trans-Ib. These compounds can be conveniently separated and isolated together when, for example, HPLC is employed for the purification.

Another embodiment of the invention relates to a process for the preparation of a racemic mixture of compounds of formulae trans-Ia and trans-Ib. In this embodiment, trans-cotininecarboxylic acid, which is defined herein as a racemic mixture of trans-IIa and trans-IIb:

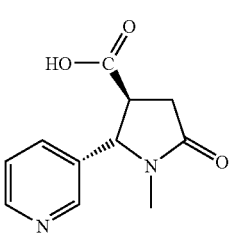

trans-IIa

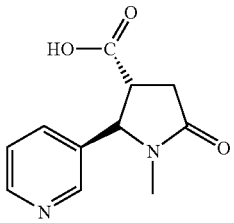

trans-IIb is reacted with an amidating reagent to yield a racemic mixture of compounds of formulae trans-IIIa and trans-IIIb:

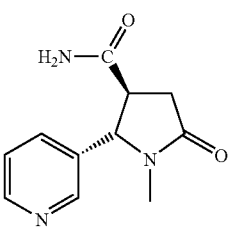

trans-IIIa

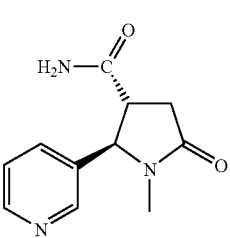

trans-IIIb

The resultant racemic mixture of compounds of formulae trans-IIIa and trans-IIIb is then reacted with a reducing agent to yield the desired racemic mixture of compounds of formulae trans-Ia and trans-Ib.

In some embodiments, the process further comprises purifying the racemic mixture of compounds of formulae trans-Ia and trans-Ib. In one embodiment, the purity of the racemic mixture is at least 95% after the purifying step. Any purification methodology is suitable. A typical method is preparative HPLC.

In the processes described above, the amidation reactions may utilize any convenient amidating reagent. Such an amidating reagent, for example, can be a combination of an activating agent of the carboxylic acid and a source of ammonium. Such combinations are well known to those who are skilled in organic synthesis, and they are described, for example, in J. March, ADVANCED ORGANIC CHEMISTRY, 5$^{th}$ ed., Wiley-Interscience (2001) and M. Bodanszky, PRINCIPLES OF PEPTIDE SYNTHESIS, 2$^{nd}$ ed, Springer-Verlag (1993). A specific example of an amidating reagent is di-t-butyl dicarbonate as activating agent in combination with ammonium bicarbonate as a source of ammonium (V. F. Pozdnev, *Tetrahedron Lett.*, 36, 7115-7118 (1995)). Amidation reactions can also be enzyme-catalyzed. Examples of enzymes promoting amidation of free carboxylic acids are lipases (Litjens et al., *Tetrahedron*, 55, 12411-12418 (1999)).

The reducing agent employed in the processes herein described is generally selected for its ability to reduce amides and lactams to amines. Many reducing agents satisfying this criterion are known to those who are skilled in organic synthesis. See J. March, supra or M. Hudlický, REDUCTIONS IN ORGANIC CHEMISTRY, $2^{nd}$ ed, ACS Monograph 188 (1996). The reducing agents include but are not limited to sources of hydride. Non-limiting examples of reducing agents include borane, alkylborane, dialkylborane, dialkylsilanes, trialkylsilanes, sodium hydride, lithium hydride, potassium hydride, and calcium hydride; complex hydrides such as lithium boron hydride, sodium boron hydride, calcium boron hydride, lithium aluminum hydride, and sodium aluminum hydride; alkoxy complex hydrides such as lithium trimethoxyaluminum hydride, lithium diethoxyaluminum hydride, lithium tri-tert-butoxyaluminum hydride, sodium bis(2-methoxyethoxy)aluminumhydride (Red-Al), and sodium trimethoxyborohydride; and alkyl complex hydrides such as lithium triethylborohydride, K-Selectride, and L-Selectride.

The following examples are provided merely to further illustrate the invention as described above. The examples are not intended to limit the scope of the invention.

EXAMPLE 1

Amidation Step (trans-IIIa and trans-IIIb)

Seventy-five grams of trans-cotininecarboxylic acid (trans-IIa and trans-IIb, 341 mmol, 1 eq.), 37.7 g of ammonium bicarbonate (477 mmol, 1.4 eq.) and 1500 mL of acetonitrile were charged to a reaction flask equipped with a thermometer, a nitrogen bubbler, an addition funnel and a mechanical stirrer. The white thick suspension was stirred for 10-15 min at room temperature (RT) before adding 13.8 mL pyridine (22.7 mmol, 0.5 eq.) in 75 mL acetonitrile. The mixture was stirred for an additional 10-15 min at room temperature before 104.1 g of di-t-butyl dicarbonate (341 mmol, 1.4 eq.) in 300 mL acetonitrile were added dropwise for 15-30 min. When this addition was complete, 37.5 mL of deionized water were added to the mixture. The reaction mixture was then stirred vigorously for 4 hours.

The reaction was considered complete when residual starting trans-cotininecarboxylic acid was present in less than 1% with respect to the formed amide as determined by high performance liquid chromatography (HPLC). At that point the batch was heated for 30-45 min at 35-45° C. and the reaction mixture was filtered through Whatman 11 μm filter paper. The filter cake was washed with acetonitrile and the filtrate collected, distilled and co-distilled with t-butyl methyl ether (TBME) and finally crystallized in TBME. The crystals were collected and washed with TBME. After drying, 83% to 94% of trans-cotinine amide (trans-IIIa/trans-IIIb) was obtained.

EXAMPLE 2

Amide Reduction Step (trans-Ia and trans-Ib)

Twelve grams of trans-cotinine amide (trans-IIIa/trans-IIIb, 1 eq.) and 758 mL toluene were charged to a reaction flask equipped with a thermometer, a nitrogen bubbler, an addition funnel and a mechanical stirrer. While applying a moderate agitation to the suspension, 74.1 mL (4.5 eq.) of a Red-Al solution in toluene (65%) were added to the mixture and stirring was continued overnight at room temperature. The progress of the reaction was monitored by HPLC. Typically more than 65% of trans-Ia/trans-Ib was formed.

The reaction was quenched by adding the mixture to a suspension of 12 g Celite and 6 g of Darco G60 charcoal in 120 mL deionized water. The quenched reaction mixture was filtered through Whatman 11 μm filter paper and the filter cake was washed with 2×24 mL of water. The filtrate was transferred to a separatory funnel and the lower aqueous layer was separated out. This aqueous layer was repeatedly coevaporated with methanol and then with toluene to obtain 19.9 g of a viscous oil after complete evaporation of the solvents. The crude mixture of trans-Ia and trans-Ib was dissolved in a minimal amount of mobile phase for the following purification step.

EXAMPLE 3

Purification Step

The following preparative chromatography system was used for purifying the crude trans-Ia and trans-Ib obtained from Example 2:

| | |
|---|---|
| HPLC System: | Varian Dynamax Preparative HPLC |
| Accessories: | One mixer unit, one sample valve, one priming valve |
| Pumps: | Two Model SD-1 (flow rates to 800 mL/min) |
| Detector: | Model UV-1 |
| Detector range: | 20 AU |
| Detector wavelength: | 260 nm |
| Purification Column: | Novasep 150 mm Ø axial compression column |
| Stationary phase: | Kromasil |
| Mobile phase: | Dichloromethane-methanol-ammonia 87:12:0.2 by volume |
| Flow rate: | 300 mL/min |
| Fraction size: | 2 min (~600 mL) |

After chromatography, each fraction was tested by HPLC to determine the percentage purity in trans-Ia/trans-Ib. Selected fractions with high purity in trans-Ia/trans-Ib were pooled. After pooling and complete solvent evaporation the chromatography yielded 26 to 35% of purified trans-Ia/trans-Ib. The purity of the trans-Ia/trans-Ib was above 97% (less than 2% cis isomer(s)).

Proton and carbon NMR analysis confirmed the structure of the purified trans-Ia/trans-Ib hapten. This was achieved by showing the presence of the pyridine ring, the pyrrolidine ring, the N-methyl group, the methylene group of the aminomethyl branch and the characteristic H-2' proton on the pyrrolidine carbon to which the pyridine ring is attached. Assignments of the chemical shifts were based on those published by T. P. Pitner et al. (The solution conformation of nicotine. A $^1$H and $^2$H nuclear magnetic resonance investigation. *J. Am. Chem. Soc.*, 100, 246-251 (1978)) for the nicotine molecule.

$^1$H-NMR (CD$_3$OD, 400 MHz): δ 8.51 (d, 1H), 8.46 (dd, 1H), 7.87 (dt, 1H), 7.43 (dq, 1H) 3.24 (m, 1H), 2.85 (d, J=8.0 Hz, 1H), 2.64 (m, 1H), 2.42 (q, 1H), 2.20 (m, 2H), 2.12 (s, 3H), 1.71 (m, 1H). $^{13}$C-NMR (CD$_3$OD, 100 MHZ): δ 149.0, 148.2, 137.8, 136.6, 124.2, 72.8, 55.4, 49.9, 43.6, 39.2, 27.0.

What is claimed is:

1. A process for the preparation of a compound of general formula I:

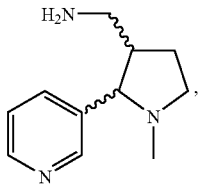

said process comprising the steps of
(a) reacting a compound of general formula II:

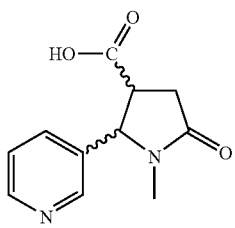

with an amidating reagent to yield a compound of general formula III:

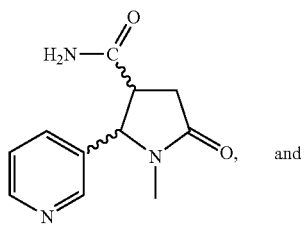

and (b) reacting said compound of general formula III with a reducing agent to yield said compound of general formula I.

2. The process according to claim 1, wherein said process further comprises the step of:
(c) purifying said compound of general formula I.

3. The process according to claim 2, wherein said process further comprises the step of:
(d) isolating said compound of general formula I as a racemic mixture of the trans isomers, formula trans-Ia and trans-Ib:

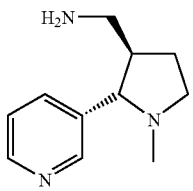
trans-Ia

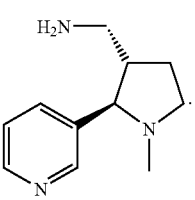
trans-Ib

4. The process according to claim 3, wherein the purity of said mixture of trans-Ia and trans-Ib is 95% or higher.

5. A process for the preparation of a racemic mixture of compounds of formulae trans-Ia and trans-Ib:

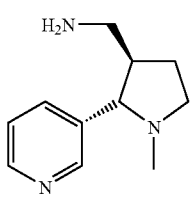
trans-Ia

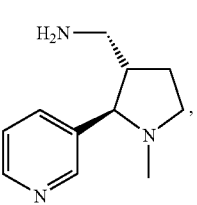
trans-Ib said process comprising the steps of
(a) reacting a racemic mixture of compounds of general formulae trans-IIa and trans-IIb:

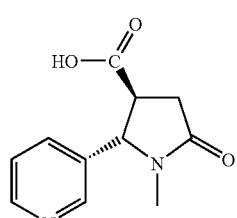
trans-IIa

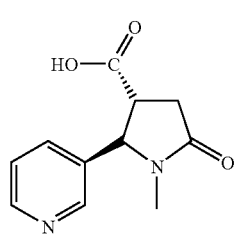
trans-IIb with an amidating reagent to yield a racemic mixture of compounds of formulae trans-IIIa and trans-IIIb:

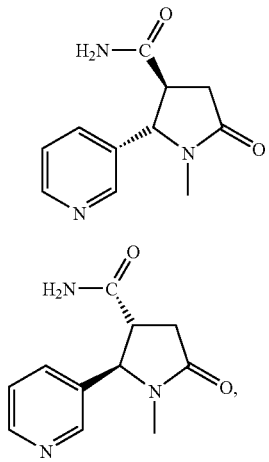
trans-IIIa

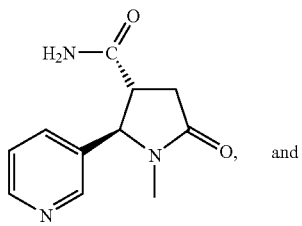
trans-IIIb
and (b) reacting said racemic mixture of compounds of formulae trans-IIIa and trans-IIIb with a reducing agent to yield said racemic mixture of compounds of formulae trans-Ia and trans-Ib.

6. The process according to claim 5, wherein said process further comprises the step of:
(c) purifying said racemic mixture of compounds of formulae trans-Ia and trans-Ib.

7. The process according to claim 6, wherein the purity of said racemic mixture of compounds of formulae trans-Ia and trans-Ib is at least 95% after said purifying step.

8. The process according to claim 6, wherein said purifying comprises subjecting said racemic mixture of compounds of formulae trans-Ia and trans-Ib to preparative high performance liquid chromatography.

9. The process according to claim 6, wherein said amidating reagent comprises a dialkyl pyrocarbonate and an ammonium salt.

10. The process according to claim 9, wherein said dialkyl pyrocarbonate is di-t-butyl dicarbonate and ammonium salt is ammonium bicarbonate.

11. The process according to claim 6, wherein said reducing reagent is a metal hydride or a complex hydride.

12. The process according to claim 11, wherein said reducing agent is a metal hydride.

13. The process according to claim 12, wherein said metal hydride is an aluminum hydride or borohydride.

14. The process according to claim 13, wherein said metal hydride is lithium aluminum hydride or sodium bis(2-methoxyethoxy)aluminum hydride.

15. A process for the preparation of a racemic mixture of compounds of formulae trans-Ia and trans-Ib:

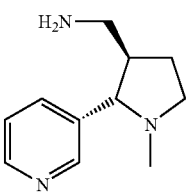
trans-Ia

-continued

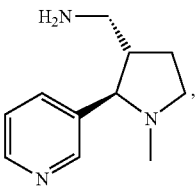
trans-Ib said process comprising the steps of:
(a) reacting a racemic mixture of compounds of general formulae trans-IIa and trans-IIb:

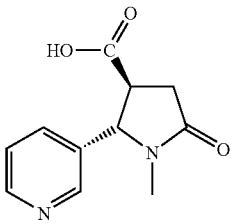
trans-IIa

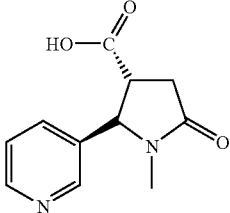
trans-IIb with an amidating reagent comprising ammonium bicarbonate and di-t-butyl dicarbonate to yield a racemic mixture of compounds of general formulae trans-IIIa and trans-IIIb:

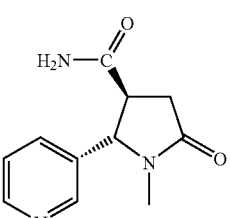
trans-IIIa

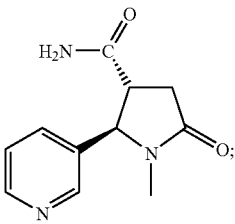
trans-IIIb (b) reacting said racemic mixture of compounds of general formulae trans-IIIa and trans-IIIb with sodium bis(2-methoxyethoxy)aluminum hydride to yield said racemic mixture of compounds of formulae trans-Ia and trans-Ib; and (c) purifying said racemic mixture that is obtained in step (b) by subjecting said racemic mixture of compounds of formulae trans-Ia and trans-Ib to preparative high performance liquid chromatography.

* * * * *